US007482506B2

(12) United States Patent
Pledger et al.

(10) Patent No.: US 7,482,506 B2
(45) Date of Patent: Jan. 27, 2009

(54) RAS P27 MOUSE MODELS AND USES THEREOF

(75) Inventors: W. Jack Pledger, Odessa, FL (US); Rosalind J. Jackson, Tampa, FL (US); Jalila Adnane, Madison, CT (US); Said M. Sebti, Tampa, FL (US)

(73) Assignee: University of South Florida, Tampa, FL (US)

( * ) Notice: Subject to any disclaimer, the term of this patent is extended or adjusted under 35 U.S.C. 154(b) by 469 days.

(21) Appl. No.: 10/472,057

(22) PCT Filed: Mar. 26, 2002

(86) PCT No.: PCT/US02/09558

§ 371 (c)(1),
(2), (4) Date: Feb. 13, 2004

(87) PCT Pub. No.: WO02/076195

PCT Pub. Date: Oct. 3, 2002

(65) Prior Publication Data

US 2004/0139484 A1 Jul. 15, 2004

Related U.S. Application Data

(60) Provisional application No. 60/278,430, filed on Mar. 26, 2001.

(51) Int. Cl.
*G01N 33/00* (2006.01)
*A01K 67/00* (2006.01)
*A01K 67/033* (2006.01)
*A01K 67/027* (2006.01)

(52) U.S. Cl. .................. 800/3; 800/13; 800/14; 800/18

(58) Field of Classification Search .............. 800/3, 800/13, 14, 18
See application file for complete search history.

(56) References Cited

U.S. PATENT DOCUMENTS

| 5,688,665 | A | 11/1997 | Massague et al. | |
| 6,180,333 | B1 | 1/2001 | Giordano | |
| 6,191,342 | B1 * | 2/2001 | Choi | 800/10 |
| 6,245,965 | B1 | 6/2001 | Roussel et al. | |
| 6,323,390 | B1 | 11/2001 | Wu et al. | |
| 6,531,645 | B1 | 3/2003 | Sebti et al. | |

FOREIGN PATENT DOCUMENTS

WO    WO 02/38751 A2    5/2002

OTHER PUBLICATIONS

Barbacid, M. "Ras oncogenes: their role in neoplasia" *Eur. J. Clin. Invest.*, 1990, 20(3):225-235.
Bos, J.L. "Ras oncogenes in human cancer a review" *Cancer Res.*, 1989, 49:4682-4689.
Downward, J. "Cell cycle: routine role for Ras" *Curr. Biol.*, 1997, 7:R258-R260.
Ewen, M.E. "Relationship between Ras pathways and cell cycle control" *Prog. Cell Cycle*, 2000 4:1-17.
Kerkhoff, E. and U.R. Rapp "Cell cycle targets of Ras/Raf signaling" *Oncogene*, 1998, 17:1457-1462.
Aktas, H. et al. "Ras links growth factor signaling to the cell cycle machinery via regulation of cyclin D1 and the Cdk inhibitor p27$^{KIP1}$" *Mol. Cell Biol.*, 1997, 17(7):3850-3857.
Arber, N. et al. "Increased expression of cyclin D1 and the RB tumor suppressor gene in c-K-ras transformed rat enterocytes" *Oncogene*, 1996, 12:1903-1908.
Filmus, J. et al. "Induction of cyclin D1 overexpression by activated ras" *Oncogene*, 1994 9:3627-3633.
Hitomi, M. and D.W. Stacey "Cellular Ras and cyclin D1 are required during different cell cycle periods in cycling NIH 3T3 cells" *Mol. Cell Biol.*, 1999 19(7):4623-4632.
Liu, J-J. et al. "Ras transformation results in an elevated level of cyclin D1 and acceleration of $G_1$ progression in NIH 3T3 cells" *Mol. Cell. Biol.*, 1995, 15(7):3654-3663.
Peeper, D.S. et al. "Ras signalling linked to the cell-cycle machinery by the retinoblastoma protein" *Nature*, 1997, 386:177-181.
Robles, A.I. et al. "Reduced skin tumor development in cyclin D1-deficient mice highlights the oncogenic ras pathway in vivo" *Genes Dev.*, 1998, 12:2469-2474.
Winston, J. et al. "Differential modulcation of $G_1$ cyclins and the Cdk inhibitor p27$^{klp1}$ by platelet-derived growth factor and plasma factors in density-arrested fibroblasts" *J. Biol. Chem.*, 1996, 271(19):11253-11260.
Sinn, E. et al. "Coexpression of MMTV/v-Ha-ras and MMTV/c-myc genes in transgenic mice: synergistic action of oncogenes in vivo" *Cell*, 1987, 22:49(4):465-475.
Fero, M.L. et al. "A syndrome of multiorgan hyperplasia with features of gigantism, tumorigenesis, and female sterility in –27$^{Klp1}$-deficient mice" *Cell*, 1996, 85(5):733-744.
Adnane, J. et al. "Loss of p21$^{WAF1/CIP1}$ accelerates Ras oncogenesis in a transgenic/knockout mammary cancer model" *Oncogene*, 2000, 19:5338-5347.

(Continued)

Primary Examiner—Anne-Marie Falk
(74) Attorney, Agent, or Firm—Saliwanchik, Lloyd & Saliwanchik

(57) ABSTRACT

The subject invention pertains to a transgenic animal model for tumorigenesis having a genome comprising a ras transgene and which is heterozygous or homozygous for a null p27 gene, and methods of using such animal to screen compounds or evaluate treatments for oncogenic and antitumor activity. The subject invention further concerns a transgenic mouse comprising a ras transgene and which has a genome that is wild-type p27$^{+/+}$, and wherein the mouse has an FVB/N and C57BL/6X 129 genetic background; and methods of using such transgenic mice to screen compounds or evaluate treatments for oncogenic or antitumor activity. Advantageously, the female animals of the subject invention are fertile and capable of nursing their young. The subject invention also pertains to in vitro systems including isolated cells or tissues of animal models for tumorigenesis, which can be used to screen compounds and treatments for oncogenic and antitumor activity.

24 Claims, 13 Drawing Sheets

OTHER PUBLICATIONS

Jackson, R.J. et al. "Loss of the cell cycle inhibitors p21$^{Cip1}$ and p27$^{Kip1}$ enhances tumorigenesis in knockout mouse models" *Oncogene,* Dec. 5, 2002, 21(55):8486-8497.

Thomas, K.R. and Capecchi, M.R. "Site-directed mutagenesis by gene targeting in mouse embryo-derived stem cells" *Cell,* 1987, 51:503-512.

Van Leeuwen, H.C. et al. "The Oct-1 POU homeodomain stabilizes the adenovirus preinitiation complex via a direct interaction with the priming protein and is displaced when the replication fork passes" *J. Biol. Chem.,* 1997, 272(6):3398-3405.

Murphy, S. "Differential in vivo activation of the class II and class III snRNA genes by the POU-specific domain of Oct-1" *Nucleic Acids Res.,* 1997, 25(11):2068-2076.

Matheos, D.D. et al. "Oct-1 enhances the in vitro replication of a mammalian autonomously replicating DNA sequence" *J. Cell. Biochem.,* 1998, 68:309-327.

Lakin, N.D. et al. "Down regulation of the octamer binding protein Oct-1 during growth arrest and differentiation of a neuronal cell line" *Mol. Brain Res.,* 1995, 28:47-54.

Hinkley, C. and Perry, M. "Histone H2B gene transcription during *Xenopus* early development requires functional cooperation between proteins bound to the CCAAT and octamer motifs" *Mol. Cell. Biol.,* 1992, 12(10):4400-4411.

Qin, X-F. et al. "Transformation by homeobox genes can be mediated by selective transcriptional repression" *The EMBO J.,* 1994, 13(24):5967-5976.

Coenjaerts, F.E.J. et al. "The Oct-1 POU domain stimulates adenovirus DNA replication by a direct interaction between the viral precursor terminal protein—DNA polymerase complex and the POU homeodomain" *The EMBO J.,* 1994, 13(22):5401-5409.

\* cited by examiner

| Mouse # | Genetic status | Background | Nursing | Pups |
|---|---|---|---|---|
| 202 | ras transgenic | FVB | No | Yes |
| 204 | ras transgenic | FVB | No | Yes |
| 206 | ras transgenic | FVB | No | Yes |
| 208 | ras transgenic | FVB | No | Yes |
| 210 | ras transgenic | FVB | No | Yes |
| 218 | ras transgenic | FVB | No | Yes |
| 220 | ras transgenic | FVB | No | Yes |
| 222 | ras transgenic | FVB | No | Yes |
| 224 | ras transgenic | FVB | No | Yes |
| 226 | ras transgenic | FVB | No | Yes |
| | | | | |
| 276F1 | ras X p27+/- | FVB X B6129/F2 | Yes | Yes |
| 278F1 | ras X p27+/- | FVB X B6129/F2 | Yes | Yes |
| 290F1 | ras X p27+/- | FVB X B6129/F2 | Yes | Yes |
| 292F1 | ras X p27+/- | FVB X B6129/F2 | Yes | Yes |
| 304F1 | ras X p27+/- | FVB X B6129/F2 | Yes | Yes |
| 306F1 | ras X p27+/- | FVB X B6129/F2 | Yes | Yes |
| 308F1 | ras X p27+/- | FVB X B6129/F2 | Yes | Yes |
| 328F1 | ras X p27+/- | FVB X B6129/F2 | Yes | Yes |
| 338F1 | ras X p27+/- | FVB X B6129/F2 | Yes | Yes |
| 352F1 | ras X p27+/- | FVB X B6129/F2 | Yes | Yes |
| 356F1 | ras X p27+/- | FVB X B6129/F2 | Yes | Yes |
| 362F1 | ras X p27+/- | FVB X B6129/F2 | Yes | Yes |
| 416F1 | ras X p27+/- | FVB X B6129/F2 | Yes | Yes |
| | | | | |
| 199F2 | ras X p27+/+ | FVB X B6129/F2 | Yes | Yes |
| 255F2 | ras X p27+/+ | FVB X B6129/F2 | Yes | Yes |
| 307F2 | ras X p27+/+ | FVB X B6129/F2 | Yes | Yes |
| 313F2 | ras X p27+/+ | FVB X B6129/F2 | Yes | Yes |
| 317F2 | ras X p27+/+ | FVB X B6129/F2 | Yes | Yes |
| 355F2 | ras X p27+/+ | FVB X B6129/F2 | Yes | Yes |
| 379F2 | ras X p27+/+ | FVB X B6129/F2 | Yes | Yes |
| 407F2 | ras X p27+/+ | FVB X B6129/F2 | Yes | Yes |
| 438F2 | ras X p27+/+ | FVB X B6129/F2 | Yes | Yes |
| 462F2 | ras X p27+/+ | FVB X B6129/F2 | Yes | Yes |
| 987F2 | ras X p27+/+ | FVB X B6129/F2 | Yes | Yes |
| 989F2 | ras X p27+/+ | FVB X B6129/F2 | Yes | Yes |

FIG. 7A

| Mouse # | Genetic status | Background | Nursing | Pups |
|---|---|---|---|---|
| 259F2 | ras X p27+/- | FVB X B6129/F2 | Yes | Yes |
| 269F2 | ras X p27+/- | FVB X B6129/F2 | Yes | Yes |
| 305F2 | ras X p27+/- | FVB X B6129/F2 | Yes | Yes |
| 321F2 | ras X p27+/- | FVB X B6129/F2 | Yes | Yes |
| 323F2 | ras X p27+/- | FVB X B6129/F2 | Yes | Yes |
| 381F2 | ras X p27+/- | FVB X B6129/F2 | Yes | Yes |
| 385F2 | ras X p27+/- | FVB X B6129/F2 | Yes | Yes |
| 405F2 | ras X p27+/- | FVB X B6129/F2 | Yes | Yes |
| 413F2 | ras X p27+/- | FVB X B6129/F2 | Yes | Yes |
| 424F2 | ras X p27+/- | FVB X B6129/F2 | Yes | Yes |
| 458F2 | ras X p27+/- | FVB X B6129/F2 | Yes | Yes |
| 461F2 | ras X p27+/- | FVB X B6129/F2 | Yes | Yes |
| 467F2 | ras X p27+/- | FVB X B6129/F2 | Yes | Yes |
| 983F2 | ras X p27+/- | FVB X B6129/F2 | Yes | Yes |
| 263F2 | ras X p27-/- | FVB X B6129/F2 | Yes | Yes |
| 351F2 | ras X p27-/- | FVB X B6129/F2 | Yes | Yes |
| 417F2 | ras X p27-/- | FVB X B6129/F2 | Yes | Yes |
| 432F2 | ras X p27-/- | FVB X B6129/F2 | Yes | Yes |
| 465F2 | ras X p27-/- | FVB X B6129/F2 | Yes | Yes |
| 488F2 | ras X p27-/- | FVB X B6129/F2 | Yes | Yes |

FIG. 7B

RAS P27 MOUSE MODELS AND USES THEREOF

CROSS-REFERENCE TO RELATED APPLICATION(S)

This application is a National Stage Application of International Application Number PCT/US02/09558, filed Mar. 26, 2002, which claims the benefit of provisional patent application Ser. No. 60/278,430, filed Mar. 26, 2001.

The subject invention was made with government support under a research project supported by National Institutes of Health Grant Nos. CA78038; CA67360; and CA67771. The government has certain rights in this invention.

BACKGROUND OF THE INVENTION

The ras oncogenes are frequently activated by point mutations or overexpression in human tumors (Barbacid, M. *Eur. J. Clin. Invest.* 1990, 20(3):225-235; Bos, J. L. *Cancer Res.* 1989, 49:4682-4689). Approximately 30% of all human tumors are associated with ras mutations and up to 95% of human pancreatic cancers contain K-ras mutations (Barbacid, M. *Eur. J. Clin. Invest.* 1990, 20(3):225-235; Bos, J. L. *Cancer Res.* 1989, 49:4682-4689). Ras proteins are believed to mediate their oncogenic effect, in part, by deregulating the cell cycle machinery (Downward, *J. Curr. Biol.* 1997, 7:R258-R260; Ewen, M. E. *Prog. Cell Cycle* 2000 4:1-17; Kerkhoff, E. and U. R. Rapp *Oncogene* 1998, 17:1457-1462). For instance, activated Ras, acting through the Raf/Mek/Erk kinase pathway, was shown to increase cyclin D1 expression and to shorten the G1 phase of the cell cycle (Aktas, H. et al. *Mol. Cell Biol.* 1997, 17:3850-3857; Arber, N. et al. *Oncogene* 1996, 12:1903-1908; Filmus, J. et al *Oncogene* 1994 9:3627-3633; Hitomi, M. and D. W. Stacey *Mol. Cell Biol.* 1999 19:4623-4632; Liu, J. J. et al. *Mol. Cell Biol.* 1995, 15:3654-3663; Peeper, D. S. et al. *Nature* 1997, 386:177-181; Robles, A. I. et al. *Genes Dev.* 1998, 12:2469-2474; Winston, J. et al., *J. Biol. Chem.* 1996, 271:11253-11260).

U.S. Pat. No. 6,191,342 describes a transgenic mouse having a genome containing the H/K-ras 4B chimeric gene to form a mammary tumor, where the mouse was prepared using an expression vector producing H/K-Ras 4B chimeric protein and having a MMTV (mouse mammary tumor virus) promoter. The expressed protein contains the first 164 amino acids of the H-Ras followed by the last 24 amino acids of K-Ras 4B.

Such MMTV/v-Ha-ras transgenic mice (Sinn E. et al., *Cell* May 1987, 22:49(4):465-475), which routinely develop mammary tumors, are used for the study of tumorigenesis and for anti-cancer drug testing. However MMTV/v-Ha-ras female mice are unable to nurse their young and, therefore, in order to breed these mice, the newborn pups must be fostered to a surrogate nursing female mouse. Usually, this fostering must be accomplished within 8 to 10 hours after birth or the survival of these newborn pups is greatly compromised. Fostering imposes significant practical and technical obstacles to breeding these mice and, therefore, impacts a researcher's ability to obtain sufficient mice for study. The obstacles include the maintenance of a sufficient number of foster male and female breeders to ensure a steady supply of nursing mothers to be used as surrogates for the newborn transgenic pups. Thus, the expense of the required foster mice must be added to the expense of the project. Also, foster mice will often not nurse the newborn transgenic pups, especially if their own pups are more than a few days old, resulting in unpredictable, expensive and wasteful loss of animals that may potentially compromise experimental results.

U.S. Pat. No. 5,688,665 discloses an isolated protein having an apparent molecular weight of about 27 kD and capable of binding to and inhibiting the activation of a cyclin E-Cdk2 complex, which is termed $p27^{KIP-1}$. U.S. Pat. No. 6,180,333 discloses methods of grading tumors and prognosticating survival rates of cancer patients by determination of p27 expression levels in tissue samples from tumors. Transgenic studies of the effect of p27 on tumorigenesis are hampered by the observation that female p27 knockout mice (Fero, M. L. et al. *Cell* May 1996, 85(5):733-744) of B6.129-cdKn1b$^{tm1MLF}$ background (also termed "C57BL/6 and 129") are sterile. Therefore, these mice inherently present husbandry challenges.

There is, therefore, a need for animal models of tumorigenesis that do not exhibit the aforementioned disadvantages and limitations. Such models would facilitate the husbandry and experimental use of transgenic models of tumorigenesis, thereby aiding in the development of treatments for tumors and the prevention of tumorigenesis. Such models would further facilitate the investigation and development of the treatment of tumorigenesis in animals having more than one transgenic gene, by eliminating husbandry problems associated with the crossing of animals that may be unable to nurse or are sterile.

BRIEF SUMMARY OF THE INVENTION

The present invention relates to animal models for tumorigenesis. Specifically, the present invention relates to transgenic animal models of tumorigenesis, in which a high proportion of the animals develop tumors within a short period of time. The present invention further concerns transgenic animals having a ras transgene within their genetic material, and which are homozygous or heterozygous for a null p27 gene (have a genotype of $p27^{+/-}$ or $p27^{-/-}$, respectively), or which are wild-type for the p27 gene ($p27^{+/+}$).

In one aspect, the present invention concerns a transgenic animal susceptible to tumor growth, or having a tumor, wherein the genome of the animal comprises a ras transgene operably linked to a promoter, and wherein the genome of the animal is also heterozygous for a p27 null gene ($p27^{+/-}$) or homozygous for a p27 null gene ($p27^{-/-}$). Thus, the genetic constitution of the transgenic animals are either ras X $p27^{+/-}$ or ras X $p27^{-/-}$. Preferably, the Ras protein is expressed within at least one tissue of the animal.

In a further aspect, the subject invention includes a female $p27^{-/-}$ animal, such as a mouse, with a genome comprising a ras transgene, and wherein the animal is fertile and capable of nursing young. In another aspect, the present invention includes a fertile female ras transgenic animal, such as a mouse, capable of nursing young, in which the genome of the animal is $p27^{+/-}$.

In another aspect, the subject invention includes a transgenic mouse that is rasxp27$^{+/+}$, with a genetic background of FVB/N and C57BL/6x 129.

In another aspect, the present invention concerns a transgenic animal susceptible to tumor growth, or having a tumor, wherein the genome of the animal comprises a mammalian H/K-ras 4B gene operably linked to a promoter, such as a mammary tumor virus (MTV) promoter, and where the genome of the mammal contains at least one null p27 gene (designated herein $p27^{+/-}$ or $p27^{-/-}$ to show the respective heterozygous and homozygous aspects of the animal's genotype). In another aspect, the present invention concerns a transgenic mouse susceptible to tumor growth, or having a tumor, wherein the genome of the mouse comprises a mammalian H/K-ras 4B gene operably linked to a promoter, such as a mammary tumor virus (MTV) promoter, and where the genome of the mammal is p27$^{+/+}$ and the mouse has a genetic background of FVB/N×C57BL/6 and 129SV. In another aspect, the present invention pertains to methods for producing the transgenic animals disclosed herein.

Preferably, the transgenic animal of the subject invention having a ras X p27$^{+/-}$ or ras X p27$^{-/-}$ genotype is a non-human vertebrate animal. More preferably, the transgenic animal of the subject invention is a mammal. Yet more preferably, the transgenic animal of the subject invention is a mammal of the order rodentia or lagomorpha. Still more preferably, the transgenic animal is a mouse, rat, or rabbit Most preferably, the transgenic animal is a mouse and the mouse has a FVB/N and C57BL/6x 129 genetic background.

In another aspect, the subject invention further concerns a method of screening a compound or treatment for oncogenic or antitumor activity by administering such a compound, or a pharmaceutically acceptable salt of such a compound, or treatment, to a transgenic animal described herein, where the genome of the animal comprises a ras transgene operably linked to a promoter so that the Ras protein is expressed within at least one tissue of the animal, and where the genome is also heterozygous or homozygous for a p27 null gene. Preferably, the transgenic animal is a mouse. More preferably, the transgenic mouse has a FVB/N×C57BL/6x 129 genetic background. Alternatively, the transgenic mouse utilized in the screening method of the subject can have ras X p27$^{+/+}$ genotype (instead of p27$^{+/-}$ or p27$^{-/-}$) with a FVB/N and C57BL/6x 129 genetic background. Following a course of therapy, efficacy can be assessed by determination of relative survival and tumor growth rates in cohorts of tumor-bearing animals that receive therapy (compounds or treatments) versus tumor-bearing animals that receive no therapy or administration of a placebo, for example.

In a further aspect, the subject invention concerns an in vitro system for screening a treatment or compound for oncogenic or antitumor activity by administering such a treatment or compound, or a pharmaceutically acceptable salt of such a compound, to the tissues or cells isolated from a transgenic animal disclosed herein. In another aspect, the subject invention pertains to methods of using such isolated cells or tissues for screening a treatment or compound for oncogenic or antitumor activity. Furthermore, the subject invention concerns methods of making such in vitro systems, which can include the steps of producing a transgenic animal model disclosed herein and isolating cells or tissue.

BRIEF DESCRIPTION OF THE DRAWINGS

FIGS. 7A and 7B show tables listing the nursing status of the original MMTV/v-Ha-ras (FVB) mice compared with the hybrid mice (FVB X C57BL/6) of the three groups, ras X p27$^{+/+}$, ras X p27$^{+/-}$, and ras X p27$^{-/-}$.

FIGS. 9A-9B show salivary and mammary tumor sizes, respectively, which was monitored weekly in ras/p27$^{+/+}$ (○) and ras/p27$^{-/-}$ (■) after the first observation of salivary and mammary tumors. Week 1 represents the first time that a particular tumor was seen and size measurements were initiated. Tumor diameters were measured in three dimensions using calipers, and tumor volumes were calculated. For salivary tumors, n=8 and 3 for ras/p27$^{+/+}$ and ras/27$^{-/-}$ mice, respectively. For mammary tumors, n=9 and 5 for ras/p27$^{+/+}$and ras/p27$^{-/-}$ mice, respectively. In FIG. 9C, ras/p27$^{+/+}$ (▲), ras/p27$^{+/-}$(□), and ras/p27$^{-/-}$ (●) mice were euthanized when tumor size reached 2 centimeters. T$_{50}$ values represent the times (in days) at which 50% of the mice in each group were sacrificed. P values are as follows: ras/p2$^{7+/+}$ versus ras/p27$^{+/-}$, 0.96; ras/p27$^{+/+}$ versus ras/p27$^{-/-}$, 0.09; and ras/p27$^{+/-}$ versus ras/p27$^{-/-}$, 0.07. Comparison of all three groups gives a p value of 0.13.

In FIG. 10B, at the time of sacrifice, a mammary carcinoma from a ras/p27$^{+/+}$ mouse (7.6 months of age) and a mammary carcinoma from a ras/p27$^{-/-}$ mouse (7.2 months of age) were fixed, sectioned, and either stained with H & E or incubated with antibody to Ki-67 and immunostained. Mitotic figures in the ras/p27$^{-/-}$tumor stained with H&E are indicated by arrows.

FIG. 11A shows a mammary tumor from a ras/p27$^{-/-}$ mouse sacrificed at 7.2 months of age, and stained with H & E. The arrow indicates the invasive carcinoma, and the (*) indicates a dilated and hyperplastic mammary duct (magnification×400). FIG. 11B shows a salivary tumor from a ras/p27$^{-/-}$ mouse sacrificed at 3.9 months of age stained with H & E (magnification×100). The arrows indicate the smooth border of the tumor. T=tumor; N=normal tissue. FIG. 11C shows the same tissue as shown in FIG. 11B, but at ×400 magnification. Myoepithelial cells (ME) and epithelioid cells (E) are indicated by arrows.

BRIEF DESCRIPTION OF THE SEQUENCES

Figure 1:
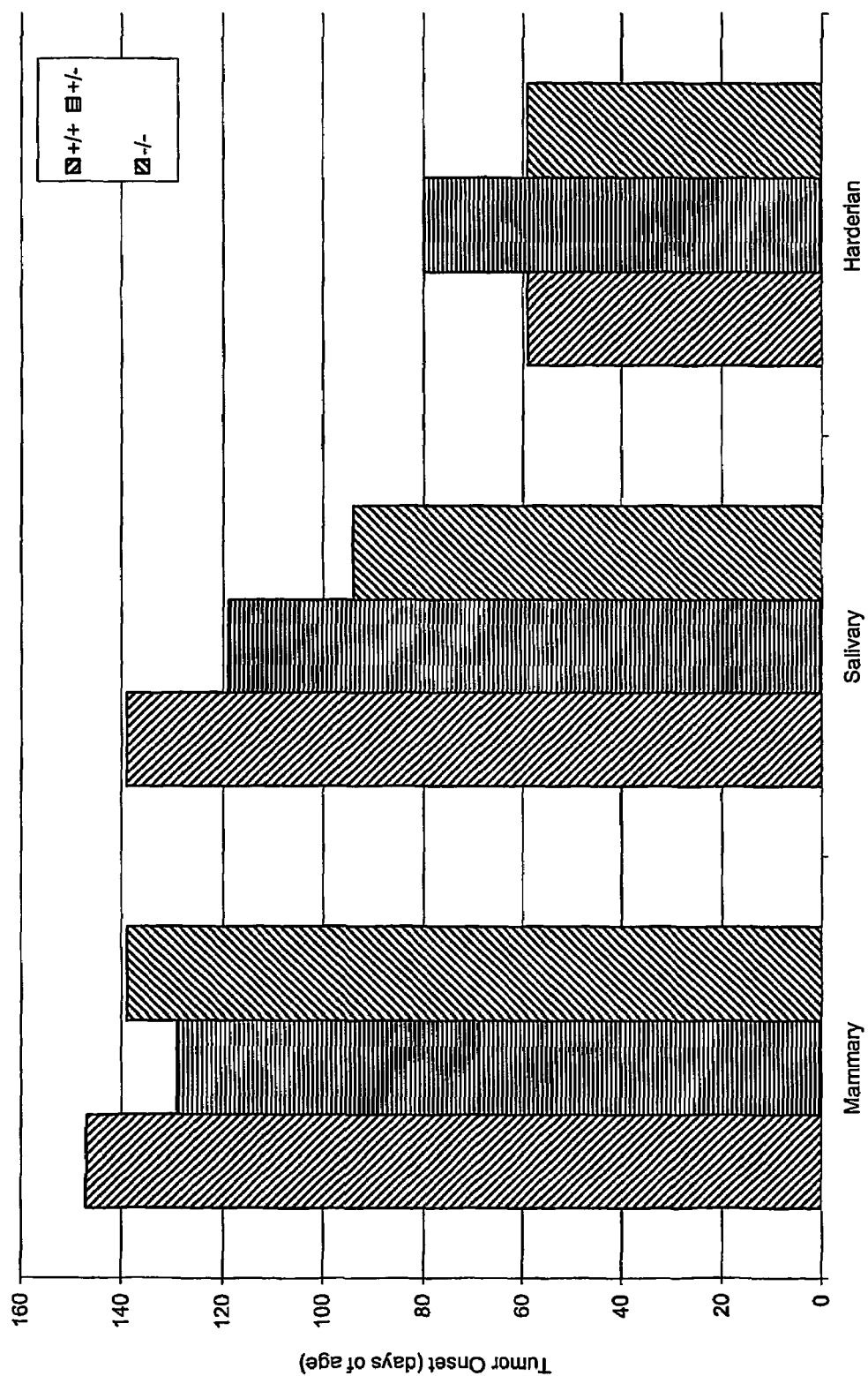
FIG. 1 is a graph which shows ras tumorigenesis (tumor onset) as affected by p27 genetic status. The graph compares tumorigenesis among the three groups of mice: ras X p27$^{+/+}$, ras X p27$^{+/-}$, and ras X p27$^{-/-}$. Tumorigenesis is not significantly affected in the ras X p27$^{+/+}$ mice when compared to the ras X p27$^{+/-}$ and ras X p27$^{-/-}$ mice.

SEQ ID NO. 1 is a v-Ha-ras-specific primer sequence used for genotyping (R-MMTV/v-Ha-ras).

SEQ ID NO. 2 is a v-Ha-ras-specific primer sequence used for genotyping (F-MMTV/v-Ha-ras).

SEQ ID NO. 3 is a p27$^{Kip1}$-specific primer sequence used for genotyping (p27K3 (common)).

SEQ ID NO. 4 is a p27$^{Kip1}$-specific primer sequence used for genotyping (p27 F-N).

SEQ ID NO. 5 is a p27$^{Kip1}$-specific primer sequence used for genotyping (p27- K5).

DETAILED DISCLOSURE OF THE INVENTION

In the present invention, an animal tumorigenesis model is disclosed that has utility in the screening of compounds for oncogenic activity, antitumorigenic activity, and/or being capable of preventing tumorigenesis. To obviate problems inherent in the use of ras transgenic mice (such as the inability of ras transgenic females to nurse their pups) and p27$^{-/-}$ mice (such as the sterility of the females), hybrid animals are bred that provide an improved model for tumorigenesis, exhibiting similar susceptibility to tumor formation yet lacking the aforementioned nursing and fertility problems.

In one aspect, the present invention concerns a transgenic animal susceptible to tumor growth, or having a tumor, wherein the genome of the animal comprises a ras transgene operably linked to a promoter, and wherein the genome of the animal is also either heterozygous or homozygous for a p27 null gene (p27$^{+/-}$ or p27$^{-/-}$ respectively). Preferably, the Ras protein is expressed within at least one tissue of the animal. In a further aspect, the subject invention includes a female p27$^{-/-}$ animal, such as a mouse, that is fertile, and the genome of which comprises a ras transgene. In another aspect, the present invention includes a female ras transgenic animal, such as a mouse, capable of lactating and nursing young, in which the genome of the animal is p27$^{+/-}$ or p27$^{-/-}$. This represents an advantage over conventional ras transgenic mice, which are presently bred in an FVB genetic background and unable to nurse their pups. Additionally, p27 knockout female mice are sterile in the currently available genetic background. Therefore, the transgenic animals of the subject invention represent a solution to this problem wherein the fertile phenotype of wild type animals is restored to female ras X p27 knockout animals.

In another aspect, the subject invention concerns a transgenic mouse with a ras transgene and of wild-type p27$^{+/+}$ genotype, and wherein the transgenic mouse is of the FVB/N and C57BL/6x 129 genetic background. Advantageously, the female mice having the ras transgene, the p27$^{+/+}$ genotype, and FVB/N and C57BL/6x 129 genetic background are fertile and capable of lactation.

In another aspect, the present invention concerns a transgenic animal with a propensity for tumor growth, or having a tumor, wherein the genome of the animal comprises a mammalian H/K-ras 4B gene operably linked to a promoter, such as a mammary tumor virus (MTV) promoter, and where the genome of the mammal contains at least one null p27 gene (designated herein p27$^{+/-}$ or p27$^{-/-}$ to show the respective heterozygous and homozygous aspects of the animal's genotype).

The transgenic animals of the subject have a propensity for developing tumors, including mammary tumors, salivary tumors, Harderian gland tumors, lung tumors, and spleen tumors. The transgenic animals of the subject invention are capable of developing tumors at a rate of at least about 0.2 cm$^3$ per week. In another aspect, the transgenic animals are capable of developing tumors at a rate of about 0.4 cm$^3$ per week. In another aspect, the transgenic animals of the invention are capable of developing tumors at a rate of about 0.6 cm$^3$ per week. In yet another embodiment, the transgenic animals of the subject invention are capable of developing tumors at a rate of at least 0.8 cm$^3$ per week. In still another aspect, the transgenic animals of the subject invention are capable of developing tumors at a rate of about 0.2 cm$^3$ per week to about 0.8 cm$^3$ per week.

In another aspect, the subject invention further concerns a method of screening a compound or treatment for oncogenic or antitumor activity by administering such a compound, or a pharmaceutically acceptable salt of such a compound, or a treatment to a transgenic animal of the present invention, where the genome of the animal comprises a ras transgene operably linked to a promoter so that the Ras protein is expressed within at least one tissue of the animal, and where the genome is also p27$^{-/-}$ or p27$^{+/-}$. Alternatively, the transgenic animal can be a mouse comprising a ras transgene operably linked to a promoter, wherein the mouse is wild-type for p27$^{+/+}$ and wherein the mouse has the FVB/N and C57BL/6x 129 genetic background. The administration step can be carried out by contacting or otherwise exposing a transgenic animal disclosed herein to a compound or treatment to be screened. Upon administration of the compound or treatment, at least one parameter in the transgenic animal can be evaluated and compared to the dosage of the compound or intensity of the treatment and the modulation of the parameter(s) in a second transgenic animal model disclosed herein which has not been exposed to the compound or treatment, as an indication of the oncogenic potential or therapeutic potential of the compound or treatment for treating the tumor.

Alternatively, upon administration of the compound or treatment, at least one physiologic parameter in the transgenic animal can be evaluated and compared to the dosage of the compound or intensity of the treatment and the modulation of the parameter(s) in a second transgenic animal disclosed herein which has been exposed to a known quantity of a known compound or a known intensity of a known treatment, as an indication of the oncogenic potential or therapeutic potential of the compound or treatment for treating a tumor.

The administration step of the method of the subject invention can be carried out before, during, or after development of a tumor. For example, the compound or treatment can be administered to the transgenic animal before, during, or after the development of an anaplasia (Goss of differentiation), dysplasia (a typical proliferation of cells characterized by nuclear enlargement and failure of maturation and differentiation, short of malignancy), or full malignancy (primary or metastasized).

Parameters can be quantitatively and/or qualitatively evaluated and can include, but are not limited to, tumor size, number of tumors, presence of tumor markers, differentiation of tumor tissue, extent of tumor cell death, and/or level of metastatic spread. Changes that occur to the parameters upon administration of the compound or treatment can include prevention, delayed onset, increase, or decrease in the parameter, for example, which can be interpreted as the animal's response to the compound or treatment.

Histologic (architectural) and gross features of malignancy can be utilized to evaluate and compare parameters, in response to a compound or treatment. For example, invasion of the underlying or surrounding tissue, stromal changes (such as desmoplasia), loss of normal structure (dedifferenitiation), creation of new structure, necrosis, angiogenesis, inflammation, and metastasis can be evaluated. In addition, tumor size and number can be determined grossly by palpation. Tumors can be classified using diagnostic electron microscopy. Immunoassays can be utilized to detect and quantify tumor markers within tissue or body fluids, such as cell surface antigens, cytoplasmic proteins, enzymes, and hormones which indicate the presence of tumor. Immunocytochemistry can be utilized to localize such tumor markers. Flow cytometry can be utilized to measure individual cell characteristics, such as membrane antigens and DNA content of tumor cells.

Preferably, the transgenic animal of the subject invention is a non-human vertebrate animal. More preferably, the transgenic animal of the subject invention is a mammal. Mammalian species which can be utilized as transgenic animals of the subject invention include, and are not limited to, apes, chimpanzees, orangutans, monkeys; domesticated animals (pets) such as dogs, cats, guinea pigs, hamsters, mice, rats, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, hyena, seals, sea lions, elephant seals, otters, porpoises, dolphins, and whales. More preferably, the transgenic animal of the subject invention is of the order rodentia or lagomorpha. Still more preferably, the transgenic animal is a mouse, rat, or rabbit Most preferably, the transgenic animal is a mouse having a FVB/N and C57BL/6x 129 genetic background.

In a further aspect, the subject invention concerns an in vitro system for screening a compound for oncogenic or antitumor activity by administering such a compound, or a pharmaceutically acceptable salt of such a compound, to the tissues or cells isolated from the animal model of tumorigenesis disclosed herein. For example, tumor cells or tissues can be isolated from the transgenic animals disclosed herein and utilized for screening purposes. In another aspect, the subject invention pertains to methods of using such isolated cells or tissues for screening a compound for oncogenic or antitumor activity, wherein the method can include the same steps described above with respect to the transgenic animals as a whole. Furthermore, the subject invention concerns methods of making such in vitro systems, which can include the steps of producing a transgenic animal disclosed herein and isolating the tumor cells or tissue.

Transgenic p27 mice of the B6.129-cdKn1b$^{tm1MLF}$ genetic background (also termed C57BL/6 and 129) are described in the scientific literature (Fero, M. L. et al. *Cell*, May 1996, 85(5):733-744 and Jackson Laboratory Catalog, 2002-2003, The Jackson Laboratory, Bar Harbor, Me., USA).

Various methods known in the art for disrupting the functional expression of a gene can be utilized to produce a p27 deficient animal. The p27 gene can be disrupted partially (such as a leaky mutation), resulting for example in reduced expression, or the p27 gene can be fully disrupted (complete ablation). Such mutations can include, for example, point mutations, such as transitions or transversions, or insertions and/or deletions. The mutation can occur in the coding region encoding p27 or merely in its regulatory sequences. Genetic changes can be carried out through selective breeding, exposure to mutagens, X-rays, or through genetic engineering for example. Genetic modifications other than that involving the p27 gene can be carried out using similar methods.

Likewise, various methods known in the art can be utilized for introducing a heterologous gene (transgene), such as the ras transgene, into the genetic material of a cell or animal (Maniatis et al. [1982] Molecular Cloning: A Laboratory Manual, Cold Spring Harbor Laboratory, New York), for purposes of producing the transgenic animals of the subject invention. The result can be a temporary or permanent alteration of genotype. Examples of genetic engineering methods that can be utilized to deliver a heterologous nucleotide include direct microinjection of nucleic acids into fertilized eggs, retroviral-mediated transgenesis, or embryonic stem cell mediated techniques. These techniques and others are detailed in the art (Hogan et al. Manipulating the Mouse Embryo, A Laboratory Manual (Cold Spring Harbor Laboratory Press, Cold Spring Harbor, 1986). Embryonic stem cell mediated techniques are described by Gossler, A. et al. (1986), *Proc. Natl. Acad. Sci. USA* 83:9065-9069; transfer of entire chromosomal segments (to produce "transnomic mice") are described by Richa and Lo (1989), *Science* 245: 175-177; gamete transfection in conjunction with in vitro fertilization is described by Lavitrano et al. (1989) *Cell* 57:717-723; and pronuclear microinjection is described by Gordon, J. W. et al. (1980) *Proc. Natl. Acad. Sci. USA* 77:7380-7384.

The transgenic animals of the subject invention can be crossed with animals having other genetic modifications to accentuate development of tumors, or to reduce development of tumors, for example.

As used herein, the term "tumor" is synonymous with the term "neoplasm" and refers to an abnormal tissue mass whose growth exceeds and is uncoordinated with that of adjacent normal tissue and persists after cessation of the stimuli that provoked it The tumor can be benign or malignant.

As used herein, the term "compound" can include any of a variety of candidate biologically or chemically synthesized substances, such as hormones, antibodies, virus, protein, peptide, amino acids, lipids, carbohydrates, nucleic acids, nucleotides, drugs, prodrugs, or other substance that may have an effect on cells, whether such effect is harmful, beneficial, a combination thereof, or otherwise. For example, immunosuppressive agents, cytostatic agents, and agents which modulate cytokine functional activity (or which potentially have one or more of these properties) can be screened. Thus, the transgenic animals of the subject invention, and isolated cells of such transgenic animals, can be used for screening agonists and antagonists of compounds and factors that affect the various metabolic pathways, for example. The animal models, and isolated cells and tissues thereof, can be exposed to the compound in a dose-escalation manner in vitro or in vivo to evaluate the effects on the cell and/or the animal, respectively. As used herein, the term "compound" is also intended to include cells which can be administered to the transgenic animals of the subject invention. The cells can be genetically modified or not genetically modified.

As used herein, the term "treatment" can include any of a variety of candidate interventions that may have either a therapeutic or beneficial effect, an oncogenic effect, or otherwise have a detrimental effect, or combinations thereof. For example, a treatment can include radiation therapy, which may have both therapeutic and detrimental effects on the transgenic animal.

All patents, patent applications, provisional applications, and publications referred to or cited herein are incorporated by reference in their entirety, including all figures and tables, to the extent they are not inconsistent with the explicit teachings of this specification.

Materials and Methods

Mouse Genotyping. The p27$^{Kip1}$ and MMTV/v-Ha-ras genotypes were analyzed by the polymerase chain reaction (PCR). Genomic DNA (gDNA) was isolated from an approximately 1 centimeters section of mouse tail using the DNEASY Tissue Kit (QIAGEN) or the method of Davis, R.

W. et al. (1980) *Methods Enzymol.* 65:404-411. The genotypes of offspring resulting from the crosses of the p27$^{-/-}$ and MMTV/v-Ha-ras mice were determined using v-Ha-ras-specific and p2$^{Kip1}$-specific primers. For v-Ha-ras and p27$^{Kip1}$ genotyping, gDNA was amplified in the presence of 1.5 mM MgCl$_2$, 0.2 mM dNTP mix, 1× QIAGEN buffer, 1 μM of each primer, and 2 U of Taq polymerase (QIAGEN). The primer sequences for v-Ha-ras were as follows: R-MMTV/v-Ha-ras (GGGCATAAGCACAGATAAAACACT) (SEQ ID NO. 1) and F-MMTV/v-Ha-ras (CCCAAGGCITAAG-TAAGTTTTGG) (SEQ ID NO. 2), which generate a fragment of 852 b.p. after incubation. PCR parameters were as follows: 95° C. for 3 min., followed by 30 cycles of 95° C. for 1 min., 55° C. for 45 sec., and 72° C. for 45 sec., and ending with primer extension at 72° C. for 10 min. For p27$^{Kip1}$, the primer sequences were: p27-K3 (common) TGGAACCCTGTGC-CATCTCTAT (SEQ ID NO. 3); p27 F-N (generates mutant fragment=800 b.p.) CCTTCTATGGCCTTCTTGACG (SEQ ID NO. 4); and p27-K5 (generates wild type garment=900 b.p.) GAGCAGACGCCCAAGAAGC (SEQ ID NO. 5). Cycling parameters were as follows: incubation at 95° C. for 3 min. followed by 40 cycles of 95° C. for 1 min., 61° C. for 45 sec., and 72° C. for 45 sec., and ending with primer extension at 72° C. for 7 min. (Adnane, J. et al. 2000 *Oncogene* 19:5338-5347).

Monitoring and Sample Collection. Monitoring and sample collection were performed as described in Adnane, J. et al. *Oncogene* 2000, 19:5338-5347. Briefly, 50 female offspring from the F2 generation (17 ras/p27$^{+/+}$, 23 ras/p27$^{+/-}$, and 10 ras/27$^{-/-}$ mice) were inspected weekly for tumors by observation and palpation. Calipers were used to measure tumor diameters in three dimensions, and tumor volumes were calculated. Animals were sacrificed when tumors reached 2 centimeters in diameter or when morbidity was noted, and necropsies were performed. Particular emphasis was placed on an examination of the salivary, mammary, and Harderian (acrimal) glands, the predominant sites of tumor formation in MMTV-v-Ha-ras mice (Sinn, E. et al. *Cell* 1987, 49:465475). The lungs, liver, kidneys, spleen, and colon were also examined for the presence of lesions. Representative samples of normal and tumor tissue were fixed in 10% neutral buffered formalin for histologic evaluation.

Histology. For general microscopy, fixed tissues were embedded in paraffin blocks, 3 μm-thick sections were cut, and slides were stained with hematoxylin and eosin (H&E) (RICHARD-ALLAN SCIENTIFIC) using standard histologic techniques. For determination of the proliferative status of Ras-induced tumors, tumor sections were incubated with an antibody to Ki-67 clone B56 (#36521A, PHARMINGEN) at a 1/400 dilution following microwave antigen retrieval with citrate buffer on an autostainer (DAKO) using the LSAB+ kit (DAKO). The percentage of apoptic cells in the same tumor sections was determined by terminal deoxynucleotidyl transferase-mediated dUTP nick-end labeling (TUNEL) using the In situ Cell Death Detection Kit (BOEHRINGER-MANNHEIM).

Statistical Analysis. Tumor frequencies in the three groups of mice (ras/27$^{+/+}$, ras/p27$^{+/-}$, and ras/p27$^{-/-}$) were compared using the Fisher's Exact Test. For quantitative variables, comparisons were made rising the Kruskal Wallis Test for more than two groups, followed by Wilcoxon Rank Sum Tests for pairs of groups. The Kruskal Wallis Test and the Wilcoxon Rank Sum Test are the non-parametric analogs of the one-way ANOVA and the pooled t test, respectively, and are more appropriate when sample sizes are small and normality uncertain. Comparisons of the survival curves for independent groups were done using the Log Rank Test. All p values are two-sided. Analyses were performed using Proc Freq, Proc Nparlway, Proc Lifetest, and Proc Lifetest of SAS (version 8).

It should be understood that the examples and embodiments described herein are for illustrative purposes only and that various modifications or changes in light thereof will be suggested to persons skilled in the art and are to be included within the spirit and purview of this application.

EXAMPLE 1

Preparation of Transgenic ras p27 Mouse Model of Tumorigenesis

Methods for preparation of ras transgenic mice (in this example, mice containing the MMTV/V-Ha-ras transgene), and phenotypic and pathological properties of the mice, including, for example, mammary, salivary, and lymphoid tissue tumorigenesis, are fully described and disclosed in Sinn, E. et al. *Cell* May 1987, 22:49(4):465-475, which is hereby incorporated in its entirety by reference.

Similarly, methods for preparation of p27$^{-/-}$ transgenic mice (in this example, mice homozygous for the targeted, disrupted p27$^{Kip-1}$ gene), and phenotypic and pathological properties of the mice, including multi-organ hyperplasia, neoplastic growth of the pituitary and tumorigenesis, are fully described and disclosed in Fero, M. L. et al. *Cell* May 1996, 85(5):733-744, which is also hereby incorporated in its entirety by reference. Polymerase chain reaction (PCR)-based screening methods for detecting the presence of one or both transgenes are also disclosed in the aforementioned two references.

Because the cross of ras transgenic males with p27$^{-/-}$ females yields no offspring, ras transgenic females were crossed with p27$^{-/-}$ males. However, because the ras transgenic females are not able to nurse, the F1 generation of p27$^{+/-}$ pups from this parental cross need to be fostered to surrogate female mice. After performing PCR to determine which females were positive for the ras transgene, these females were crossed with littermate males who were ras negative, which was also determined by PCR analysis.

It is not necessary to use foster mothers for the newborn offspring of the F1 generation ras-positive female mice (all p27 heterozygous), or for any additional generations of these mice (regardless of their p27 genetic status). The ras transgenic, p27$^{-/-}$ crossed female mice are no longer sterile.

More specifically, MMTV/v-Ha-ras transgenic females (FVB background, Charles River Labs, Wilmington, Mass.) were crossed with p27$^{-/-}$ mice, 129×C57/B6jF2 hybrids (obtained from James Roberts, Fred Hutchinson Cancer Research Center, Seattle, Wash.). The females from the F1 and all following generations of these MMTV/v-Ha-ras transgenic mice (regardless of their p27 genetic status) developed mammary tumors as expected for MMTV/v-Ha-ras females, but were also able to nurse their young, eliminating the need to foster newborn pups. Even after these ras transgenic females developed mammary tumors, they still had lactating mammary glands and were able to nurse their pups successfully. The ability of these ras transgenic females to nurse their young offers a significant technical advantage in breeding ras transgenic animals, and in using the animals for the study of, for example, tumorigenesis and for anti-cancer drug testing.

Additionally, while p27$^{-/-}$ female mice are sterile, the MMTV/v-Ha-ras X p27$^{-/-}$ cross females are fertile and give birth to live pups. Since all females can be used for breeding regardless of their p27 status, littermate crosses are much easier to carry out. The p27$^{-/-}$ pups are generated more efficiently since the breeder females can be homozygous knockouts.

The ability of female mice to nurse the pups is shown in the table of FIG. 7 as a function of their genetic status. FIG. 7 shows a list of the original MMTV/v-Ha-ras mice (FVB) obtained from Charles River Labs, which are unable to nurse. These female mice (ras transgenic males are sterile) were crossed with p27$^{-/-}$ males (B6.129/F2) to obtain the heterozygous F1 generation of ras X p27$^{+/-}$. (Mice who are not positive for the ras transgene were not used.) Ras positive F2 offspring, from the F1 littermate crosses, were analyzed for their p27 status and were mated in order to promote tumor development from the MMTV promoter. As shown, both the F1 and F2 females, including the ras X p27$^{-/-}$ females, were able to have pups and to nurse. The majority of these mice and essentially all of these F1 and F2 mice were able to nurse since it is found that it is no longer necessary to foster the pups. The mice in all cases had litters containing an average of 8-10 pups.

Figure 2:
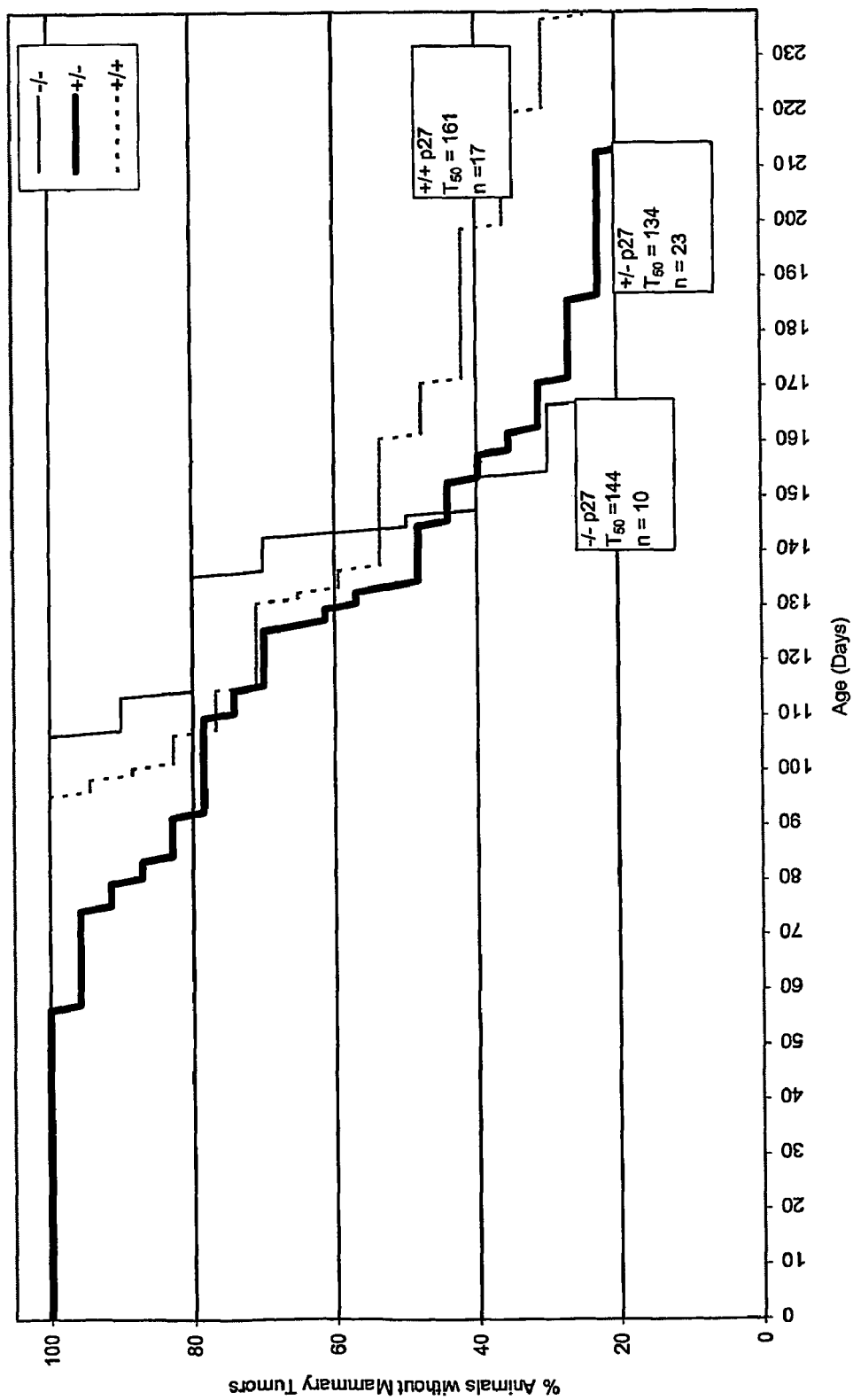
FIG. 2 is a graph which shows the percentage of mice that are free of mammary tumors as a function of age and genetic status.
Figure 3:
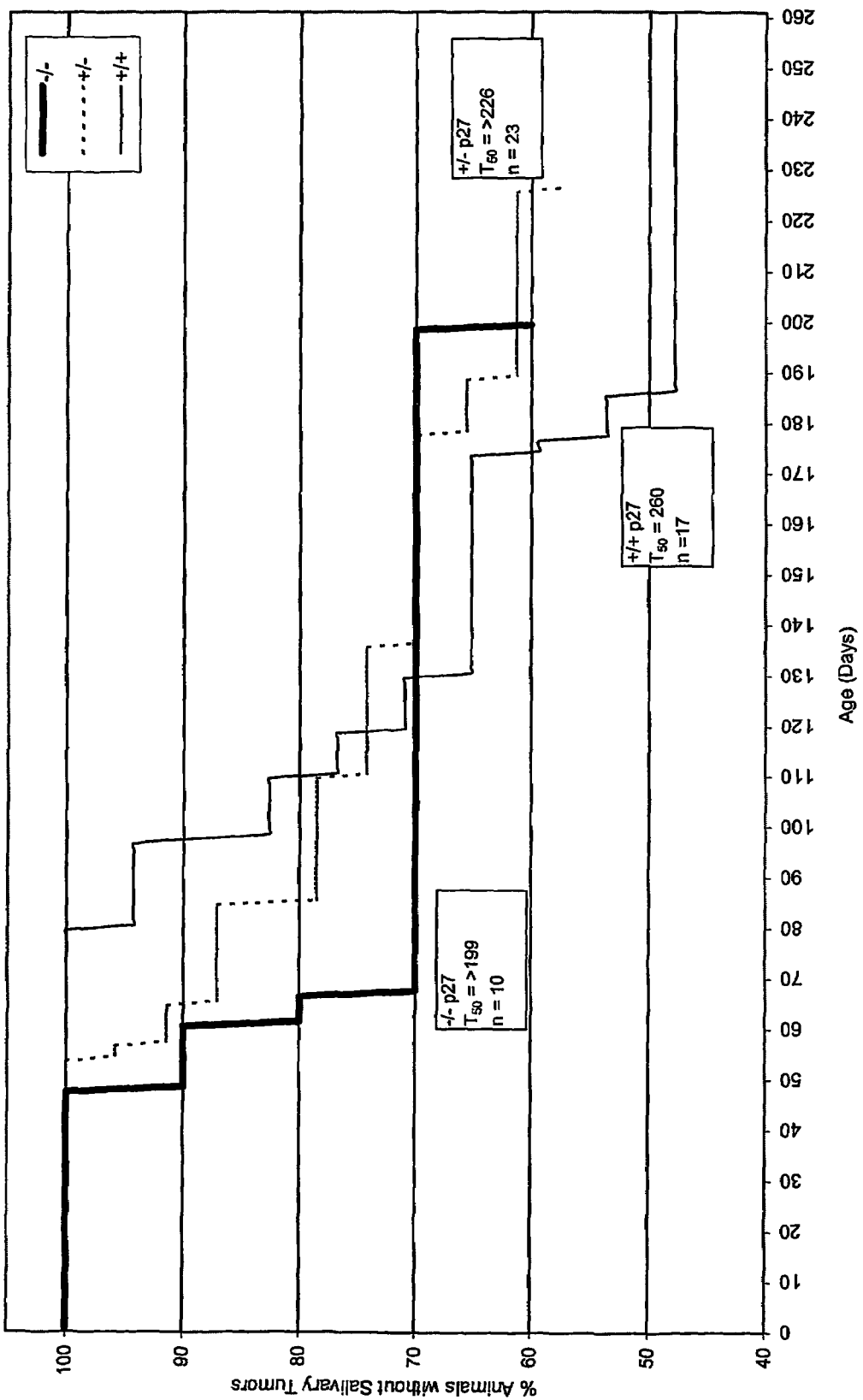
FIG. 3 is a graph which shows the percentage of mice that are free of salivary tumors as a function of age and genetic status.
Figure 4:
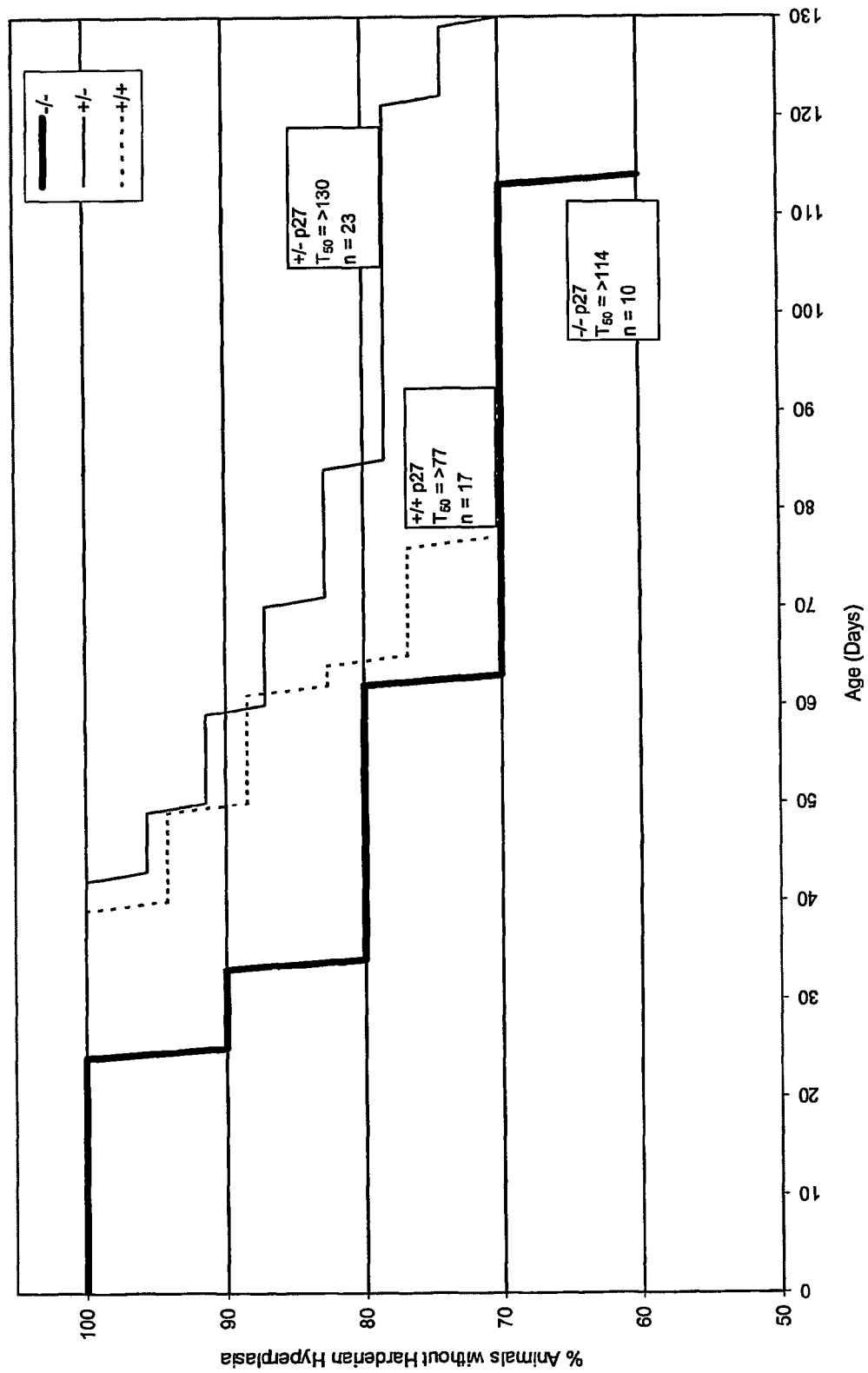
FIG. 4 is a graph which shows the percentage of mice that are free of Harderian Hyperplasia as a function of age and genetic status.
Figure 5:
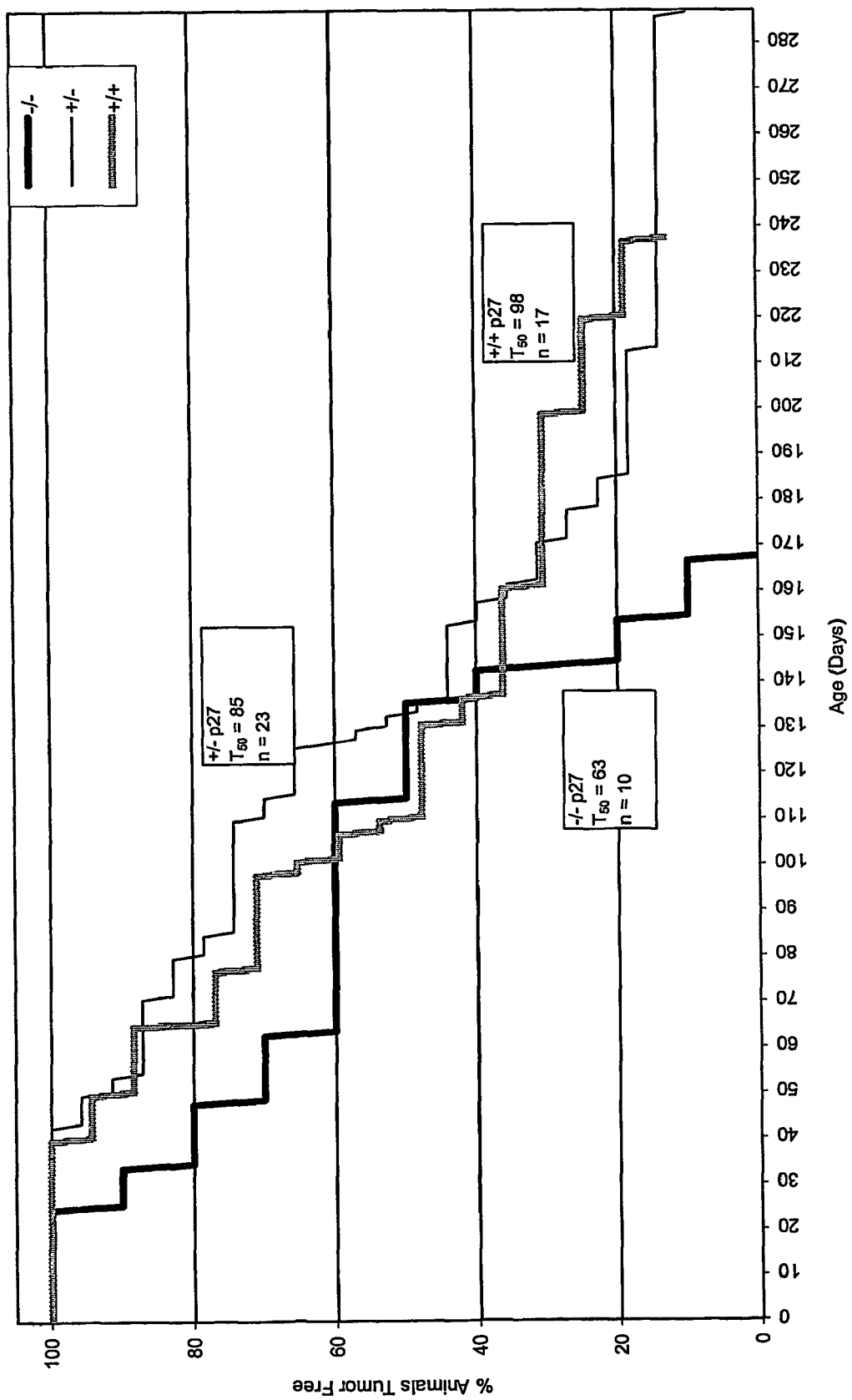
FIG. 5 is a graph which shows the percentage of mice that are totally free of tumors as a function of age and genetic status.
Figure 6:
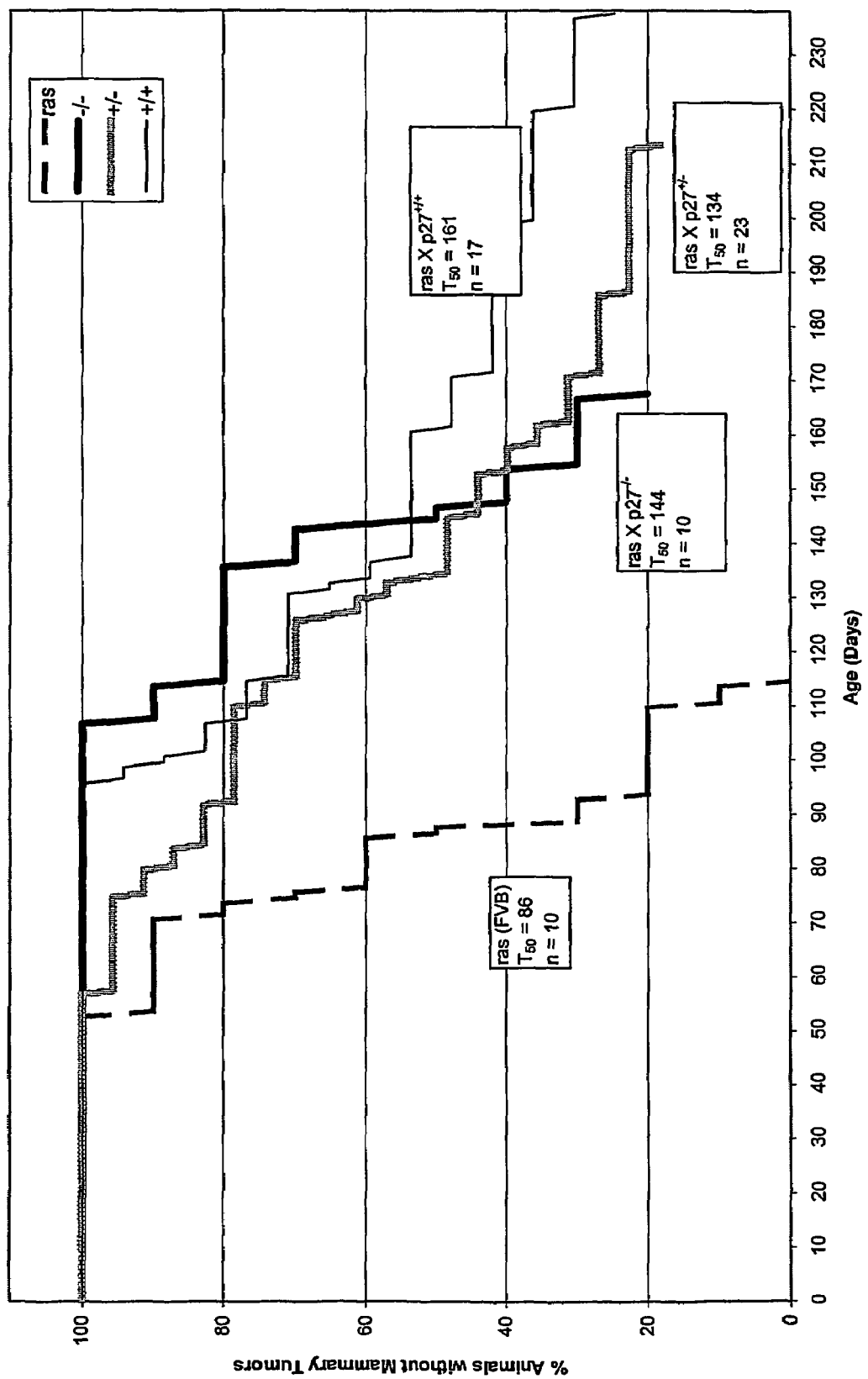
FIG. 6 is a graph which compares the percentage of mice that are free of mammary tumors as a function of age and genetic status in ras mice with and without a p27 knockout gene.

Tumorigenesis within the ras X p27$^{+/-}$ and ras X p27$^{-/-}$ mice is substantially similar to tumorigenesis within the ras breeder mice. Furthermore, the ras X p27$^{+/-}$ mice can nurse and ras X p27$^{-/-}$ female mice, unlike the female p2$^{-/-}$ breeder mice, are fertile. Thus, the ras X p27$^{+/-}$ and ras X p27$^{-/-}$ mice lack the aforementioned disadvantages of the breeder ras and p27$^{-/-}$ mice, yet retain utility as models for tumorigenesis. Thus, FIG. 1 shows that the time for tumor onset for mammary, salivary, and Harderian tumors is substantially unaffected by the p27 status of ras transgenic mice of the present invention. The graphs shown in FIGS. 2-4 depict this observation as a time-course for tumor development for mammary tumors, salivary tumors, and Harderian hyperplasia, respectively. The graph in FIG. 5 combines these data for all forms of tumors. The graph shown in FIG. 6 compares tumor onset in ras (FVB) breeder mice (p27$^{+/+}$), with ras X p27$^{+/-}$ and ras X p27$^{-/-}$ mice. While tumor onset is somewhat delayed compared to the breeder mice, the mice of the present invention retain utility as models for the study and development of treatments for tumorigenesis.

EXAMPLE 2

Effects of p27$^{Kip1}$ Loss on Tumor Formation in Mice Expressing v-Ha-Ras

Figure 8:
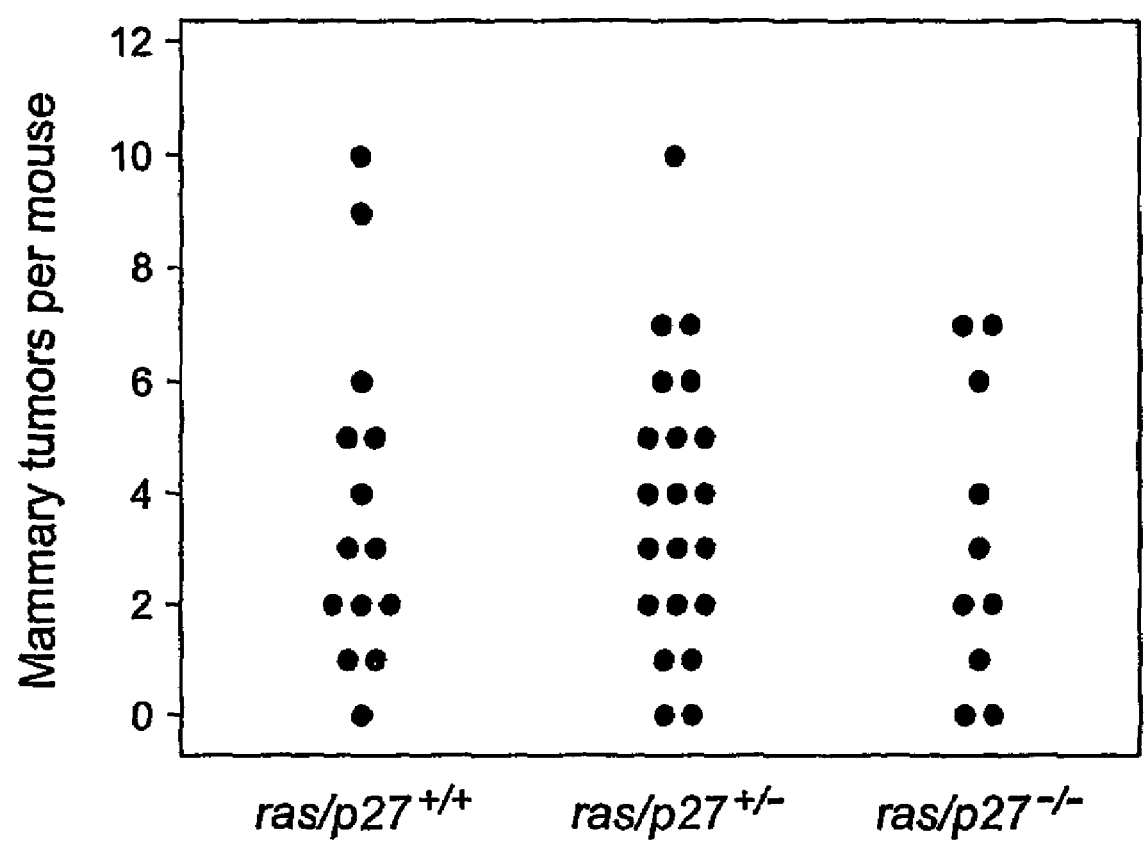
FIG. 8 shows the number of tumors per mouse, determined weekly by observation and palpation. The numbers shown represent the final number of tumors per mouse prior to sacrifice. Mice were sacrificed throughout the examination period whenever tumor size reached 2 centimeters or when signs of morbidity were detected.

Experiments were performed on MMTV/v-Ha-ras mice expressing different dosages of the p27$^{Kip1}$ gene. ras/27$^{+/+}$, ras/p27$^{+/-}$, and ras/p27$^{-/-}$ were generated and monitored weekly for tumor formation by observation and palpation. As described by Sinn, E. et al. *Cell* 1987, 49:465-475, MMTV/v-Ha-ras mice spontaneously develop salivary and mammary adenocarcinomas and benign Harderian gland hyperplasias, all of which are easily detected externally. The times at which ras/2$^{+/+}$, ras/p27$^{+/-}$, and ras/p27$^{-/-}$ mice developed salivary, mammary, or Harderian gland tumors are shown in FIGS. 1-6. Most mice in all three groups developed mammary tumors, whereas salivary and Harderian gland tumors were less frequent. P27$^{Kip1}$ had no effect on tumor onset; regardless of tumor type. Tumor multiplicities (as determined for salivary and mammary tumors) were also similar in the three groups of mice, as shown in FIG. 8. For example, the average numbers of mammary tumors per tumor-positive mouse at the time of sacrifice were 4.1 (ras/27$^{+/+}$), 4.2 (ras/p27$^{+/-}$, and 4.0 (ras/p27$^{-/-}$. Therefore, unlike p21$^{Cip1/-}$, p27$^{Kip1}$ does not affect the timing of tumor formation or the number of tumors formed in mice expressing the v-Ha-ras transgene.

Figures 9A, 9B:
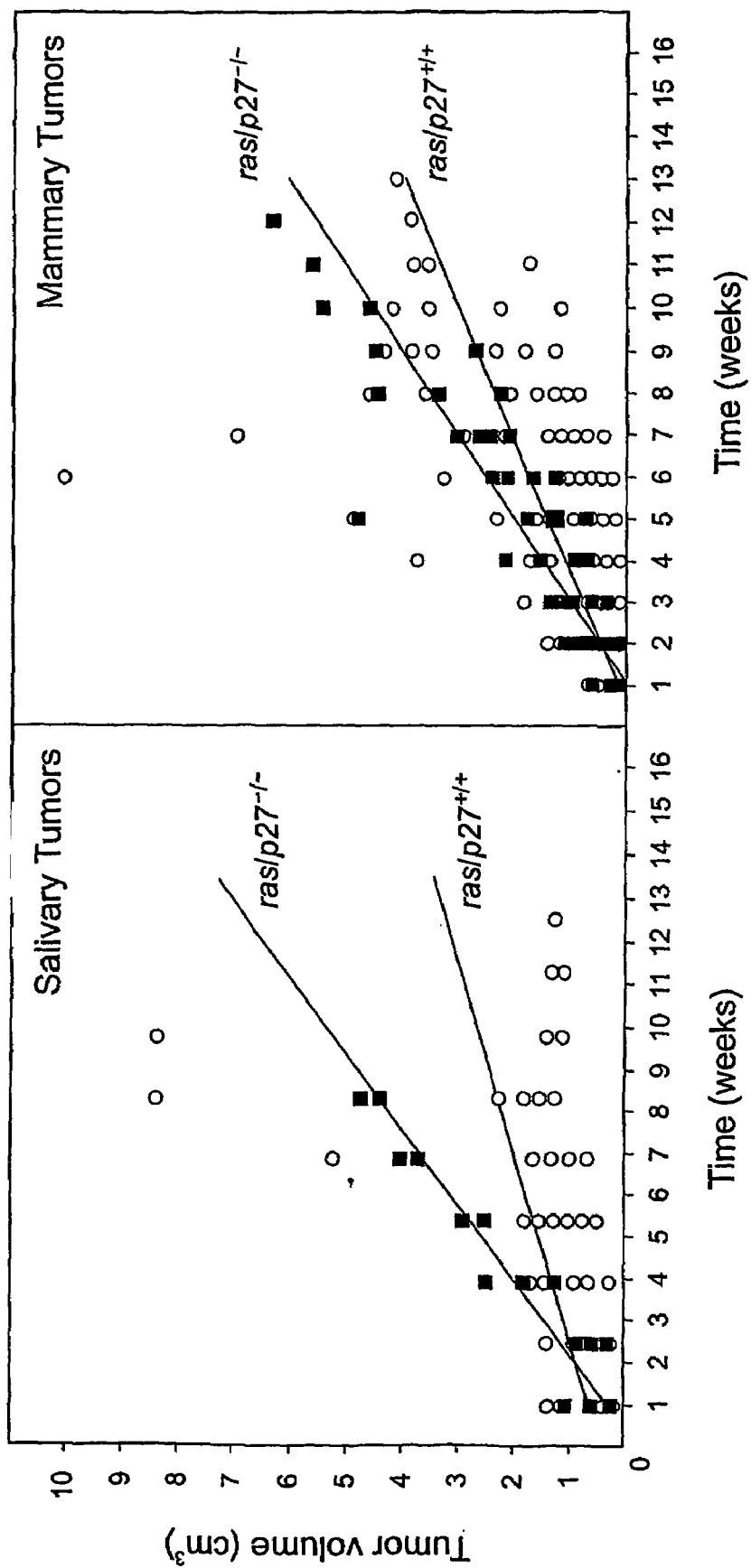
FIGS. 9A-9C show tumor growth rates in ras/27$^{+/+}$, ras/p27$^{+/-}$, and ras/p27$^{-/-}$ mice.
Figure 9C:
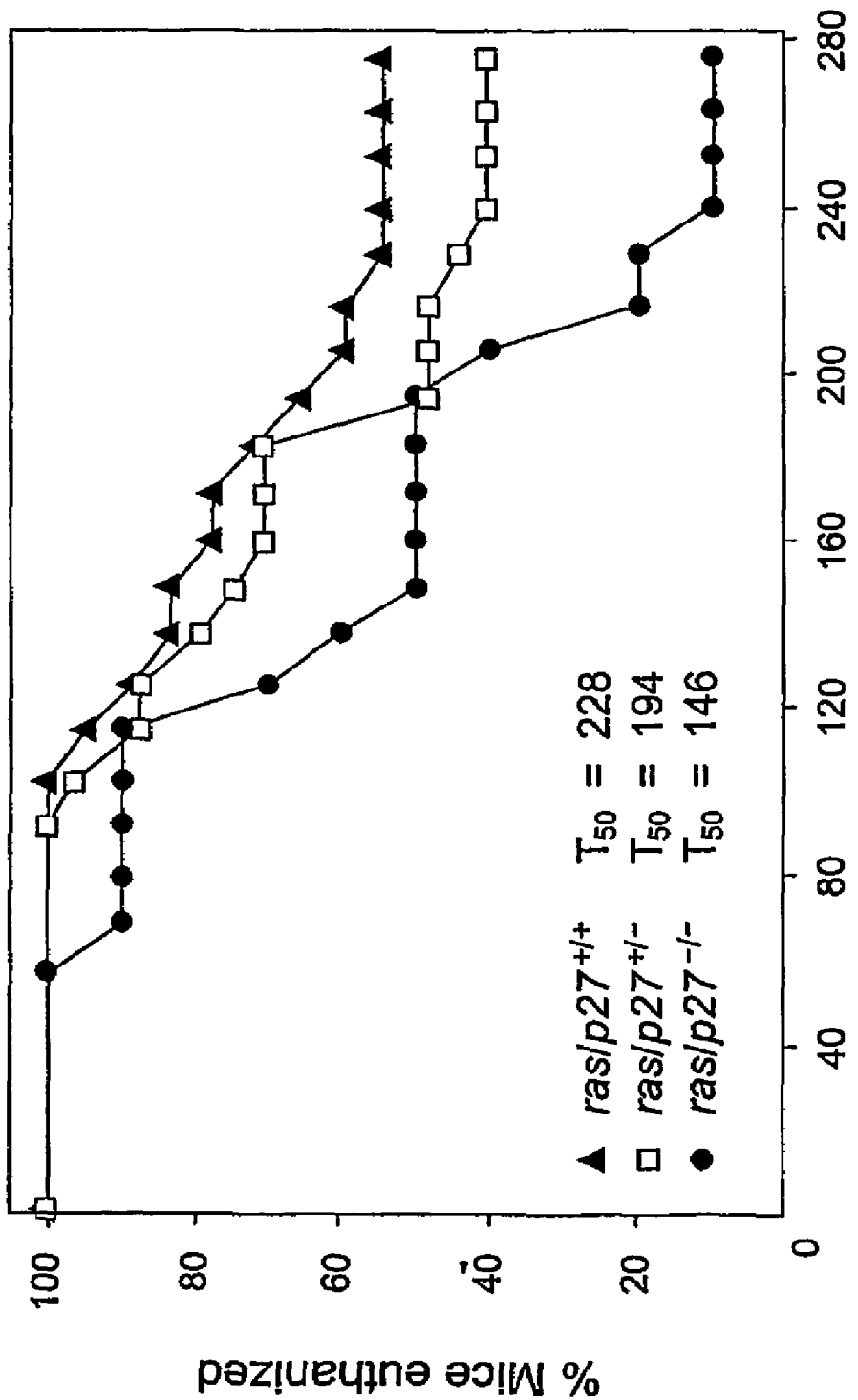
Figure 10A:
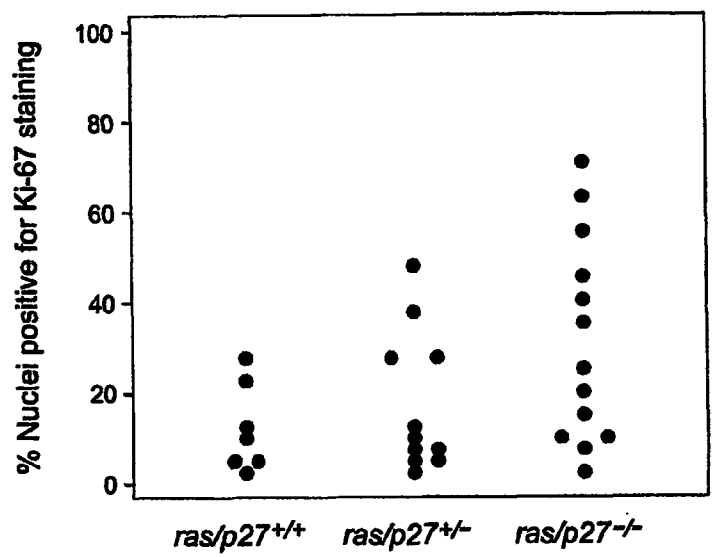
FIGS. 10A and 10B show the proliferative index in tumors of ras/27$^{+/+}$, ras/p27$^{+/-}$, and ras/p27$^{-/-}$ mice. Salivary and mammary tumors were isolated from ras/p27$^{+/+}$, ras/p27$^{+/-}$, and ras/p27$^{-/-}$ mice sacrificed at various times when tumors measured 2 centimeters or when mice showed signs of morbidity. Formalin-fixed tumor sections were incubated with antibody to Ki-67 and immunostained as described in Materials and Methods. The percentage of stained nuclei was determined.
Figure 10B:
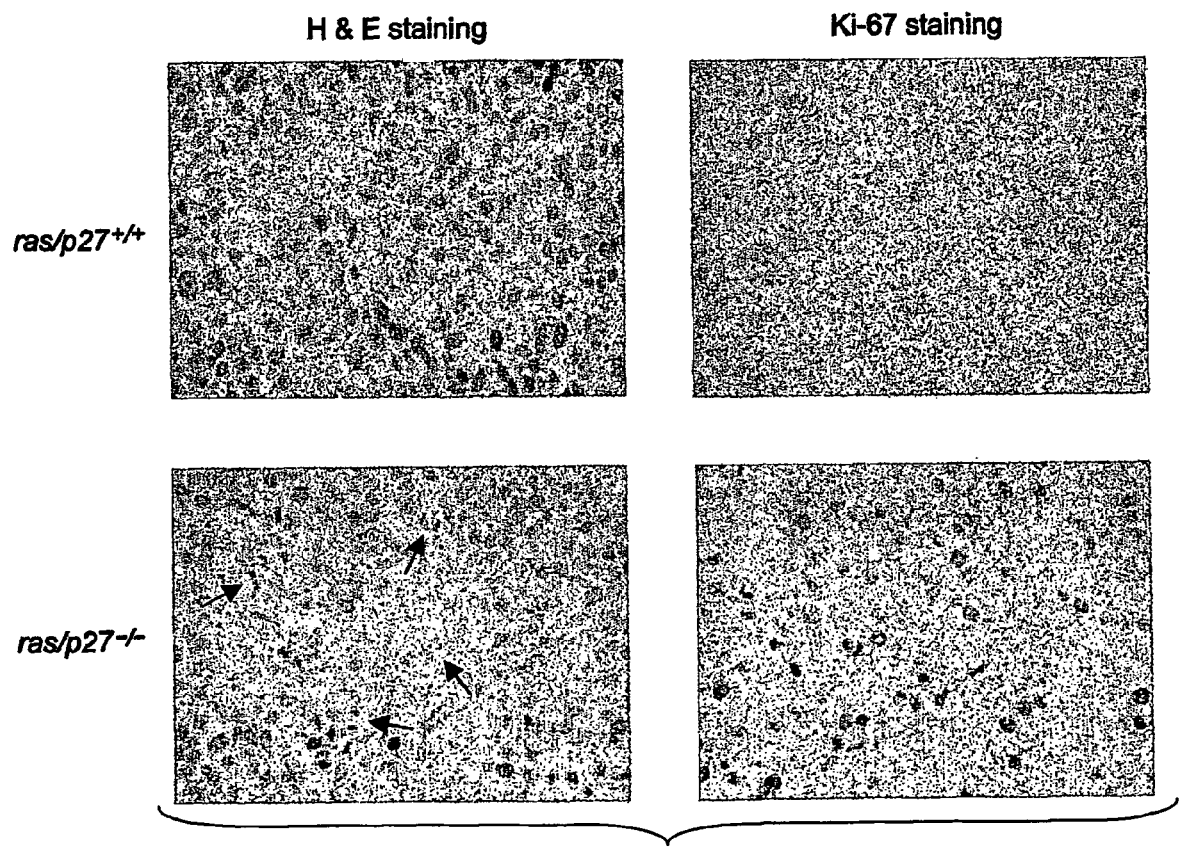
Figure 11A:
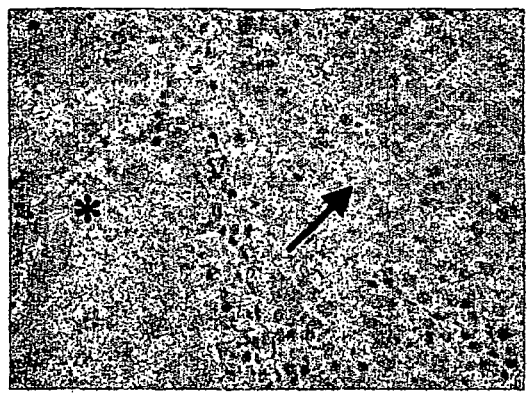
FIGS. 11A-11C show the characteristic features of aggressive tumors in ras/p27$^{-/-}$ mice.
Figure 11B:
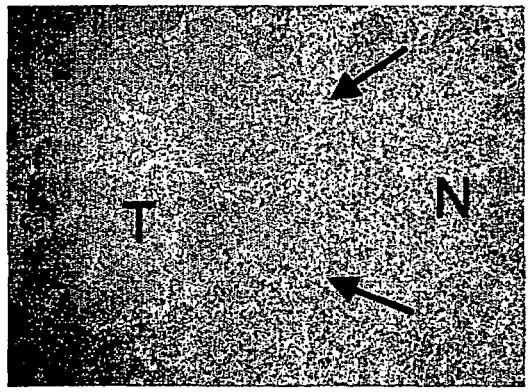
Figure 11C:
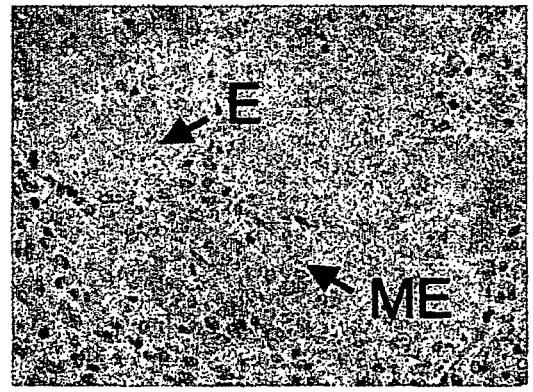

When tumors in intact mice were measured in three dimensions, and tumor volumes were calculated, clear and significant increases in growth rates were observed for both salivary and mammary tumors in ras/p27$^{-/-}$ as compared with ras/p27$^{+/+}$ mice, as shown in FIG. 9A. Growth rates for salivary tumors in ras/p27$^{+/+}$ and ras/p2$^{-/-}$ mice were 0.247 and 0.811 cm$^3$ per week, respectively (p=0.0001), and growth rates for mammary tumors in ras/p27$^{+/+}$ and ras/p27$^{-/-}$ mice were 0.403 and 0.546 cm$^3$ per week, respectively (p=0.016). Salivary tumors grew at similar rates in ras/p27$^{+/-}$ and ras/p27$^{-/-}$ mice, whereas mammary tumors grew at similar rates in ras/p27$^{+/-}$ and ras/27$^{+/+}$ mice (data not shown). Harderian tumors were too small to be measured accurately. As an alternative way of assessing tumor growth rate, the times at which tumor sized reached 2 centimeters in any dimension was plotted; in accordance with National Institutes of Health (NIH) guidelines, mice were sacrificed at this time. The times at which 50% of the mice in each group were euthanized (T$_{50}$ values) were determined. As listed in FIG. 9C, T$_{50}$ values were 228, 194, and 146 days for ras/p27$^{++}$, ras/p27$^{+/-}$, and ras/p27$^{-/-}$ mice, respectively. The differences between the T$_{50}$ values for ras/p27$^{-/-}$ and ras/p27$^{+/+}$ mice were statistically significant (p=0.09), as were those for ras/p27$^{-/-}$ and ras/p27$^{+/-}$ mice (p=0.07).

EXAMPLE 3

Screening Antitumor Compounds or Treatments

To screen a compound for oncogenic activity, antitumor activity and/or the capability of preventing tumorigenesis, the compound can be administered to the transgenic animals of the present invention in the form of a pharmaceutically acceptable salt in a pharmaceutically acceptable carrier. Administration can be intramuscular, intraperitoneal, oral, anal, inhalation, topical, or by any other route known to those of skill in the art Dosage can be varied to develop a dose-response curve based on a variety of physiologic parameters, and tumor development may be monitored as a function of dosage. Likewise, treatments such as radiation therapy can be administered to the transgenic animal and various physiologic parameters can be evaluated and compared to treatment intensity, frequency, and other experimental variables.

The invention claimed is:

1. A transgenic mouse having a genome comprising a ras transgene operably linked to a promoter, wherein said genome is p27$^{+/-}$ or p27$^{-/-}$, wherein said mouse develops tumors, and wherein a female transgenic mouse is able to nurse mouse pups.

2. The transgenic mouse of claim 1, wherein said ras transgene is a mammalian H/K-ras 4B gene.

3. The transgenic mouse of claim 1, wherein said promoter is a mammary tumor virus promoter.

4. The transgenic mouse of claim 1, wherein said promoter is a mouse mammary tumor virus promoter.

5. The transgenic mouse of claim 1, wherein the transgenic animal has a tumor selected from the group consisting of a mammary tumor, salivary tumor, Harderian gland tumor, lung tumor, and spleen tumor.

6. The transgenic mouse of claim 1, in which said p27 null gene is p27$^{Kip-1}$.

7. The transgenic mouse of claim 1, in which said p27 null gene is lacking exons 1 and 2.

8. The transgenic mouse of claim 1, wherein the transgenic mouse is a fertile female.

9. The transgenic mouse of claim 1, wherein said ras transgene is a mammalian H/K-ras 4B gene, and wherein said promoter is a mouse mammary tumor virus promoter.

10. The transgenic mouse of claim 9, wherein the mouse has a mixed FVB/N and C57BL/6x 129 genetic background.

11. The transgenic mouse of claim 1, wherein said ras transgene is expressed to produce a Ras protein.

12. The transgenic mouse of claim 1, wherein the transgenic mouse is capable of developing tumors at a rate of at least about 0.2 cm$^3$ per week.

13. The transgenic mouse of claim 1, wherein the transgenic mouse is capable of developing tumors at a rate of at least about 0.4 cm$^3$ per week.

14. The transgenic mouse of claim 1, wherein the transgenic mouse is capable of developing tumors at a rate of at least about 0.6 cm³ per week.

15. The transgenic mouse of claim 1, wherein the transgenic mouse is capable of developing tumors at a rate of at least about 0.8 cm³ per week.

16. The transgenic mouse of claim 1, wherein the transgenic mouse is capable of developing tumors at a rate of about 0.2 cm³ per week to about 0.8 cm³ per week.

17. A method of screening a compound or treatment for oncogenic or antitumor activity, said method comprising:
   administering said compound or treatment to a transgenic mouse having a genome comprising a ras transgene operably linked to a promoter, wherein said genome is $p27^{+/-}$ or $p27^{-/-}$, wherein said mouse develops tumors, and wherein a female transgenic mouse is able to nurse mouse pups; and
   evaluating the effect of said compound or treatment on one or more physiologic parameters within said transgenic mouse to determine oncogenic or antitumor activity of said compound.

18. The method according to claim 17, wherein the transgenic mouse has a mixed FVB/N and C57BL/6x 129 genetic background.

19. The method according to claim 17, wherein the transgenic mouse has a tumor selected from the group consisting of a mammary tumor, salivary tumor, Harderian gland tumor, lung tumor, and spleen tumor.

20. The method according to claim 17, wherein said ras transgene is a mammalian H/K-ras 4B gene, and wherein said promoter is a mouse mammary tumor virus promoter.

21. The transgenic mouse of claim 1, wherein the transgenic mouse has a mixed FVB/N and C57BL/6x 129 genetic background.

22. The transgenic mouse of claim 1, wherein the transgenic mouse has a tumor.

23. The method according to claim 17, wherein the transgenic mouse has a tumor.

24. The method according to claim 17, wherein said one or more physiologic parameters is selected from the group consisting of tumor size, number of tumors, presence of tumor markers, differentiation of tumor tissue, extent of tumor cell death, and level of metastasis of the tumor.

* * * * *

UNITED STATES PATENT AND TRADEMARK OFFICE
CERTIFICATE OF CORRECTION

PATENT NO. : 7,482,506 B2
APPLICATION NO. : 10/472057
DATED : January 27, 2009
INVENTOR(S) : W. Jack Pledger et al.

Page 1 of 1

It is certified that error appears in the above-identified patent and that said Letters Patent is hereby corrected as shown below:

Column 6,
Line 43, "(Goss of differentiation)" should read --(loss of differentiation)--.

Column 8,
Line 26, "provoked it The" should read --provoked it. The--.

Column 9,
Line 10, "(CCCAAGGCITAAGTAAGTTTTGG)" should read --(CCCAAGGCTTAAGTAAGTTTTGG)--.
Line 37, "(acrimal)" should read --(lacrimal)--.

Column 12,
Line 49, "the art Dosage can" should read --the art. Dosage can--.

Signed and Sealed this

Fifteenth Day of September, 2009

David J. Kappos
*Director of the United States Patent and Trademark Office*

SEQUENCE LISTING

<160> NUMBER OF SEQ ID NOS: 5

<210> SEQ ID NO 1
<211> LENGTH: 24
<212> TYPE: DNA
<213> ORGANISM: Artificial Sequence -continued

```
<220> FEATURE:
<223> OTHER INFORMATION: Oligonucleotide primer

<400> SEQUENCE: 1
gggcataagc acagataaaa cact                                              24

<210> SEQ ID NO 2
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 2
cccaaggctt aagtaagttt ttgg                                              24

<210> SEQ ID NO 3
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 3
tggaaccctg tgccatctct at                                                22

<210> SEQ ID NO 4
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 4
ccttctatgg ccttcttgac g                                                 21

<210> SEQ ID NO 5
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 5
gagcagacgc ccaagaagc                                                    19
```